United States Patent
Hundt et al.

(10) Patent No.: US 11,622,561 B2
(45) Date of Patent: Apr. 11, 2023

(54) FRUIT AND VEGETABLE-BASED FERMENTATE COMPOSITIONS AND METHODS OF MAKING AND USING THE SAME

(71) Applicant: Third Wave Bioactives, LLC, Wauwatosa, WI (US)

(72) Inventors: Matthew Hundt, Brookfield, WI (US); Brett Thompson, Kansas City, MO (US)

(73) Assignee: Third Wave Bioactives, LLC, Wauwatosa, WI (US)

( * ) Notice: Subject to any disclaimer, the term of this patent is extended or adjusted under 35 U.S.C. 154(b) by 220 days.

(21) Appl. No.: 16/760,211

(22) PCT Filed: Jan. 14, 2019

(86) PCT No.: PCT/US2019/013510
§ 371 (c)(1),
(2) Date: Apr. 29, 2020

(87) PCT Pub. No.: WO2019/143566
PCT Pub. Date: Jul. 25, 2019

(65) Prior Publication Data
US 2021/0176994 A1    Jun. 17, 2021

Related U.S. Application Data (60) Provisional application No. 62/618,875, filed on Jan. 18, 2018.

(51) Int. Cl.
| | |
|---|---|
| C12P 7/06 | (2006.01) |
| C12P 7/52 | (2006.01) |
| C12P 7/54 | (2006.01) |
| C12P 7/56 | (2006.01) |
| C12P 7/625 | (2022.01) |
| A01N 63/50 | (2020.01) |
| A01N 63/20 | (2020.01) |
| A23L 19/00 | (2016.01) |
| A23L 23/00 | (2016.01) |
| A01N 63/32 | (2020.01) |
| A23L 3/3472 | (2006.01) |
| A23L 3/3571 | (2006.01) |

(52) U.S. Cl.
CPC ............ *A01N 63/50* (2020.01); *A01N 63/20* (2020.01); *A01N 63/32* (2020.01); *A23L 3/3472* (2013.01); *A23L 3/3571* (2013.01); *A23L 19/01* (2016.08); *A23L 23/00* (2016.08); *C12P 7/065* (2013.01); *C12P 7/52* (2013.01); *C12P 7/54* (2013.01); *C12P 7/56* (2013.01); *C12P 7/625* (2013.01); *A23V 2002/00* (2013.01); *A23Y 2220/67* (2013.01); *A23Y 2220/71* (2013.01); *A23Y 2240/41* (2013.01); *A23Y 2320/25* (2013.01)

(58) Field of Classification Search
CPC .... C12P 7/065; C12P 7/52; C12P 7/54; C12P 7/56
See application file for complete search history.

(56) References Cited

U.S. PATENT DOCUMENTS

| | | | |
|---|---|---|---|
| 5,096,718 | A | 3/1992 | Ayres et al. |
| 9,441,257 | B2 * | 9/2016 | Choi .................... A23L 3/3463 |
| 9,961,914 | B2 | 5/2018 | Sliekers et al. |
| 10,040,833 | B2 | 8/2018 | Sliekers et al. |
| 10,765,131 | B2 | 9/2020 | Dierdorp-Andreae et al. |
| 2009/0226571 | A1 | 9/2009 | Freyer et al. |
| 2011/0189147 | A1 | 8/2011 | Garner et al. |
| 2015/0045288 | A1 | 2/2015 | Mygind et al. |

FOREIGN PATENT DOCUMENTS

| | | |
|---|---|---|
| CN | 103610213 A | 3/2014 |
| CN | 104585827 A | 5/2015 |
| CN | 107048139 A | 8/2017 |
| JP | 4918412 | 4/2012 |

(Continued)

OTHER PUBLICATIONS

Dimitrovski et al., "Apple juice as a medium for fermentation by the probiotic Lactobacillus plantarum PCS 26 strain", Ann Microbiology, (2015) 65: 2161-2170, DOI 10.1007/s13213-015-1056-7 (Year: 2015).*
https://en.wikipedia.org/wiki/Apple_juice (Year: 2022).*
Examination report in corresponding GB Application No. GB2010955.9 dated Jan. 11, 2022.
Extended European search report in corresponding EP Application No. 19741573.0 dated Aug. 23, 2021.
Examination Report for UK Patent Application No. GB2010955.9, dated Apr. 6, 2022.

(Continued)

*Primary Examiner* — Ruth A Davis
(74) *Attorney, Agent, or Firm* — Andrus Intellectual Property Law, LLP (57) ABSTRACT

A method for producing a fermentate including the steps of obtaining a fruit or vegetable extract, treating the extract with a hydrolytic enzyme, mixing the extract with a fermenting microorganism, water, and a growth media to produce a liquid composition; and incubating the liquid composition at a controlled temperature and a controlled pH to produce a fermentate. A method for killing or inhibiting the growth of a contaminating microorganism on or within a food product, and a food product including a fermentate having a cellular mass component from a fermenting microorganism, a fermented fruit or vegetable extract and a hydrolytic enzyme are disclosed. A fermentate produced by any one of the methods described is contemplated. The fermentate may be a concentrated liquid or a dry powder and has the ability to inhibit the growth of a contaminating microorganism by 100% when diluted to less than 5% (w/v).

13 Claims, 1 Drawing Sheet

(56) References Cited

FOREIGN PATENT DOCUMENTS

| KR | 20120051616 A | 5/2012 |
| KR | 10-1439321 | 9/2014 |
| WO | 2016081872 | 5/2016 |

OTHER PUBLICATIONS (SFGATE), "The pH Levels of Apple, Orange, Grape and Cranberry Fruit Juices", Healthy Eating, Nov. 2018, 1 retrieved from the internet: <URL: https://healthyeating.sfgate.com/ph-levels-apple-orange-grape-cranberry-fruit-juices-12062.html>.
International Search Report and Written Opinion in corresponding International Application No. PCT/US2019/013510 mailed Jun. 20, 2019.

* cited by examiner

FRUIT AND VEGETABLE-BASED FERMENTATE COMPOSITIONS AND METHODS OF MAKING AND USING THE SAME

CROSS-REFERENCE TO RELATED APPLICATIONS

This application claims priority from U.S. Provisional Application 62/618,875 filed Jan. 18, 2018, and PCT/US2019/013510, filed Jan. 14, 2019, the content of which is incorporated herein by reference in its entirety.

BACKGROUND

The Background and Summary are provided to introduce a foundation and selection of concepts that are further described below in the Detailed Description. The Background and Summary are not intended to identify key or essential features of the claimed subject matter, nor are they intended to be used as an aid in limiting the scope of the claimed subject matter.

Consumer demand for fewer and more recognizable ingredients has led ingredient suppliers to find creative ways to remove artificial ingredients and replace them with friendlier, more natural alternatives. Familiarity is one key aspect ingredient producers must consider when generating such solutions. Several ingredient manufacturers market and sell a variety of flavor and antimicrobial products based on fermentation. Today, these products involve culturing food-grade bacteria (Generally Regarded As Safe (GRAS)) on various substrates, such as sucrose, dextrose, whey, non-fat dry milk, wheat flour, and wheat starch. The resulting fermented products are labeled as "cultured wheat flour", "cultured skim milk", etc., and are subsequently added to foods to improve flavor and/or to provide improved shelf-life and food safety. These are often viewed as "label-friendly" (or, "clean label") alternatives to synthetic preservatives (such as potassium sorbate, sodium benzoate, calcium propionate, etc.).

While these ingredients make perfect sense when used in fresh dairy products and baked goods, they also contain allergens and make little sense in other applications, such as soups, dips, dressings and meat products. Additionally, consumers may be less familiar with an ingredient like "dextrose" and might question why "cultured dextrose", for example, would be included as a component of a refrigerated soup. In addition to allergenicity, these "cultured" products also often have a flavor profile that—while better than that of synthetic preservatives—may not be entirely in line with the foods within which they're being utilized. Finally, some of the fermented technologies that exist today are not allowed in all food categories, limiting their use by default. Given these limitations, there is a need in the art for preservative products that are easily recognizable by consumers, lack allergens, and provide minimal, if not improved, sensory impact.

SUMMARY

In one aspect of the present invention, fermentates are provided. The fermentates may include a cellular mass component from a fermenting microorganism and a fruit or vegetable extract component.

In another aspect, the present invention relates to methods for producing a fermentate.

Such methods may include (a) obtaining a fruit or vegetable extract, (b) mixing the fruit or vegetable extract with a fermenting microorganism, water, and a growth media capable of supporting the growth of the fermenting microorganism to produce a liquid composition, and (c) incubating the liquid composition at a controlled temperature and a controlled pH to produce a fermentate.

In a further aspect, food products are provided. The food products may include any one of the fermentates disclosed herein.

In a still further aspect, the present invention relates to methods for killing or inhibiting the growth of a contaminating microorganism on or within a food product. Such methods may include making or obtaining any one of the fermentates disclosed herein; and applying an effective amount of the fermentate to at least one surface of the food product so as to kill or inhibit the growth of the contaminating microorganism on the food product.

Various other features, objects and advantages of the disclosure will be made apparent from the following description taken together with the drawing.

DETAILED DESCRIPTION

Here, in the non-limiting Examples, the present inventors have surprisingly discovered that culturing various fruit and vegetable extracts with antimicrobial-producing bacteria (such as from the genus *Lactococcus, Lactobacillus, Pediococcus* and *Propionibacterium*) can produce effective antimicrobial fermentates. The inventors envision that the disclosed fruit and vegetable based fermentates would allow food manufacturers to use preservative products that have efficacious antimicrobial activity while also allowing for more recognizable labeling, reduced risk of allergens, and improved flavor. For example, labeling of food products including the certain of the disclosed fermentates may read "cultured onion" or "cultured potato," which would be more appealing or recognizable in a food product, which might already contain such vegetables.

Fermentate Compositions

In one aspect of the present invention, fermentates are provided. As used herein, a "fermentate" refers to a complex mixture produced by a controlled fermentation process. The fermentate, when isolated, may include a cellular mass component from a microorganism including, without limitation, fermentation end-products, metabolites, and/or unused substrates, but is devoid of viable cells. The present application contemplates a fermentate produced by any one of the methods described herein.

The fermentates may include a cellular mass component from a fermenting microorganism and a fermented fruit or vegetable extract. In some embodiments, the fermentate may be made or produced by any one of the methods for producing a fermentate disclosed herein.

As used herein, the "cellular mass component" refers to the proteins, lipids (i.e., membranes), carbohydrates, metabolites, etc., or any subset of these substances from the fermenting microorganism. For example, as a fermenting microorganism grows it produces new cells that generally include additional cellular mass such as, without limitation, cell membranes, nucleic acids (i.e., DNA and/or RNA)

internal subcellular structures, small molecules such as organic acids, or proteins (i.e., membrane-bound, secreted, and/or intracellular). The cellular mass component may include all of these substances or only some of these substances. For example, after isolation a fermentate may be treated so as to remove some of these substances such as cell membranes but retain other substances such as small molecules including, without limitation, organic acids and/or small peptides.

Accordingly, in some embodiments, the cellular mass component may include lactic acid, lactate, propionic acid, acetic acid, ethanol, an antimicrobial substance (i.e., antimicrobial peptides), or any combinations thereof. Lactic acid, lactate, propionic acid, acetic acid, and ethanol are common fermentation end-products produced by the fermentation of a fermentable carbohydrate by many Lactic Acid Bacteria and/or Propionibacteria and thus may be present in some embodiments of the fermentates disclosed herein. Ethanol may be at a concentration in the disclosed fermentates between about 0.01 mM and about 500 mM or any range therein. Lactic acid may be at a concentration in the disclosed fermentates between about 0.01 mM and about 500 mM or any range therein. Lactate, e.g. calcium lactate, sodium lactate, potassium lactate, etc., may be at a concentration in the disclosed fermentates between about 0.01 mM and about 500 mM or any range therein. Propionic acid may be at a concentration in the disclosed fermentates between about 0.01 mM and about 500 mM or any range therein. Propionate, e.g. calcium propionate, sodium propionate, potassium propionate, etc., may be at a concentration in the disclosed fermentates between about 0.01 mM and about 500 mM or any range therein. Acetic acid may be at a concentration in the disclosed fermentates between about 0.01 mM and about 500 mM or any range therein. Acetate, e.g., sodium acetate, potassium acetate, etc., may be at a concentration in the disclosed fermentates between about 0.01 mM and about 500 mM or any range therein.

As used herein, a "fermenting microorganism" refers to a microorganism that can ferment a carbohydrate source to antimicrobial substances. The fermenting microorganism may be a Lactic Acid Bacterium or a *Propionibacterium*. Suitable fermenting microorganisms may include, without limitation, a *Lactococcus* species, a *Lactobacillus* species, a *Streptococcus* species, a *Pediococcus* species, a *Propionibacterium* species, or combinations thereof. Suitable fermenting microorganisms from these species may include, without limitation, *Lactococcus lactis, Lactobacillus acidophilus, Lactobacillus brevis, Lactobacillus plantarum, Lactobacillus reuteri, Lactobacillus sakei, Propionibacterium freudenreichii, Propionibacterium acidipropionici, Pediococcus acidilactici*, or combinations thereof.

As used herein, a "fermented fruit or vegetable extract" refers to the remaining substances in a fruit or vegetable extract after fermentation by a fermenting microorganism. The fermented fruit or vegetable extract may include all of these substances or only some of these substances. For example, a fermentate may be treated so as to remove some of the substances within a fermented fruit or vegetable extract but retain other substances. The fermented fruit or vegetable extract may be, without limitation, fermented onion extract, fermented sweet potato extract, fermented celery extract, fermented carrot extract, fermented chick pea extract, fermented tomato extract, fermented spinach extract, fermented pear extract, fermented pea extract, or fermented apple extract.

As used herein, a "fruit or vegetable extract" refers to an extract from a fruit or vegetable that has been created using a man-directed process. The fruit or vegetable extract may be prepared, for example and without limitation, by squeezing, juicing, pulping, grinding, peeling, drying or powdering processes on a fruit or vegetable. Suitably, the fruit or vegetable extract may include a source of fermentable carbohydrates that may be used by the fermenting microorganism. Suitable fruit or vegetable extracts may include, without limitation, onion extract, sweet potato extract, celery extract, carrot extract, chick pea extract, tomato extract, spinach extract, pear extract, pea extract, and apple extract.

The disclosed fermentates may further include a fermented yeast extract. As used herein, a "fermented yeast extract" refers to the remaining substances in a yeast extract after fermentation by a fermenting microorganism. The fermented yeast extract may include all of these substances or only some of these substances. For example, a fermentate may be treated so as to remove some of the substances within a fermented yeast extract but retain other substances. Suitable fermented yeast extracts may be derived from yeast extracts such as, without limitation, Fischer BioReagents™ Yeast Extract, Ohly® CTT-R, Biorigin Bionis® YE MF and Procelys Springer® 0600/0-MG-L. Alternatively, the disclosed fermentates may further include a different option for obtaining nitrogen and/or vitamins such as ammonia, pea protein, corn steep liquor, and other sources readily recognizable to those of ordinary skill in the art.

As described in the non-limiting Examples, the present inventors found that some fruit and vegetable extracts did not ferment well with some fermenting microorganisms. In such embodiments, the inventors discovered that pretreatment of the fruit and vegetable extract with a hydrolytic enzyme was effective in producing sufficient fermentable carbohydrates. Accordingly, in some embodiments, the disclosed fermentates may further include a hydrolytic enzyme either in active or inactive (i.e, denatured) form. As used herein, a "hydrolytic enzyme" may include, without limitation, a cellulase, a hemicellulase, a glucanase, a xylanase, or an amylase.

In some embodiments, the disclosed fermentates have the ability to inhibit the growth of a contaminating microorganism by 100%, 90%, 80%, 70%, 60%, or 50% when diluted to less than 10%, 8%, 5%, 4%, 3%, 2%, or 1% (weight/volume of final product formulation (w/v)). To determine the antimicrobial activity of the fermentate, the contaminating microorganism may be grown in appropriate growth media to a sufficient level and diluted to between 0.5-1.0 McFarland. 10% (1 gram) of fermentate material is added to 10 ml of appropriate growth media for the contaminating microorganism strain. The sample is mixed and 5 mls may be transferred to a new tube containing 5 mls of growth media. This dilution process continues until there are treated tubes with fermentate concentrations ranging from 10% to 0.039% at half-fold intervals (10%, 5%, 2.5%, 1.25%, 0.625%, 0.312%, 0.156%, 0.078%, 0.039%). Approximately 1% (v/v) from the diluted culture sample was added to all the fermentate tubes. It is also added to one 5 ml tube that contains growth media but no fermentate (positive control). After 24 hours the growth of the positive control tube is compared to the growth in the fermentate tubes by measuring their optical densities, recorded at 600 nm. A fermentate with sufficient antimicrobial activity will be able to inhibit the growth of the contaminating microorganism by 100%, 90%, 80%, 70%, 60%, or 50% when diluted to less than 10%, 8%, 5%, 4%, 3%, 2%, 1%, 0.5%, 0.1%, or 0.05% (w/v).

In some embodiments, the fermentates may be further processed to produce a concentrated liquid or a dry powder.

Methods of concentrating fermentates to produce concentrated liquids and/or dry powders are generally known in the art. For example, the disclosed fermentates may be evaporated using a falling film or similar system or may be spray-dried on a Buchi B-290 spray dryer.

The disclosed fermentates may have a pH between about 2 and about 10 or any range therein. Suitably, the pH of the fermentate is between about 3 and about 8.

Methods for Producing a Fermentate

In another aspect, the present invention relates to methods for producing a fermentate. The methods may include (a) obtaining a fruit or vegetable extract, (b) mixing the fruit or vegetable extract with a fermenting microorganism, water, and a growth media capable of supporting the growth of the fermenting microorganism to produce a liquid composition, and (c) incubating the liquid composition at a controlled temperature and a controlled pH to produce a fermentate. The fermentate is then isolated from the liquid composition such that the fermentate may be devoid of viable cells. As explained herein, the fermentate, however, may continue to include cellular mass components. In certain embodiments, cellular mass components may be partially or completely removed from the fermentate.

Optionally, in some embodiments, the growth media capable of supporting the growth of the fermenting microorganism may include a yeast extract. Alternatively, the present inventors have discovered that the fruit or vegetable extract may serve not only as the source of a fermentable carbohydrate but may also be a growth media capable of supporting the growth of the fermenting microorganism. Accordingly, in some embodiments, the growth media capable of supporting the growth of the fermenting microorganism may be the fruit or vegetable extract.

In some embodiments, the methods for producing a fermentate may further include evaporating the fermentate to produce a second fermentate. Methods of evaporating fermentates to produce concentrated liquids are generally known in the art. For example, evaporation step may be performed using a falling film or similar system.

In some embodiments, the methods for producing a fermentate may further include spray-drying the second fermentate to produce a powdered fermentate. Methods of spray-drying fermentates are generally known in the art. For example, the present inventors disclose in the non-limiting Examples that the disclosed fermentates may be spray-dried on a Buchi B-290 spray dryer.

The present methods for producing a fermentate may be performed (i.e., incubated) under anaerobic or aerobic conditions. The anaerobic conditions may be effectuated, without limitation, using Nitrogen gas which may be sparged through the media or set to gas over the headspace of the fermentation vessel.

The present methods for producing a fermentate may further include treating the fruit or vegetable extract with a hydrolytic enzyme prior to or simultaneously with step (b) of the present methods for producing a fermentate. In some embodiments, the fruit or vegetable extract may be treated for at least 0.1, 0.2, 0.3, 0.5, 0.7, 0.8, 1, 1.5, 2, or more hours. Suitably, the fruit or vegetable extract is treated for between 0.1 and 1 hour.

In some embodiments, the present methods for producing a fermentate may further include clarifying the fruit or vegetable extract prior to or simultaneously with step (b) of the present methods for producing a fermentate. In some embodiments, the fruit or vegetable extract is clarified before, after, or simultaneously with treatment with a hydrolytic enzyme. As used herein, the term "clarifying" or "clarified" refers to the removal of large solids from, for example, an extract. The fruit or vegetable extract may be clarified by, without limitation, filtration, flocculation, sedimentation, or centrifugation.

The "controlled temperature" of the present methods may be between about 10° C. and about 60° C. or any range therein. Suitably, the controlled temperature may be between about 10° C. and about 50° C.

The "controlled pH" of the present methods may be between about 2 and about 11 or any range therein. Suitably, the controlled pH is between about 3 and about 10.

The present application contemplates a method for producing a fermentate, the method including the steps of obtaining a fruit or vegetable extract, treating the fruit or vegetable extract with a hydrolytic enzyme, mixing the fruit or vegetable extract with a fermenting microorganism, water, and a growth media capable of supporting the growth of the fermenting microorganism to produce a liquid composition; or incubating the liquid composition at a controlled temperature and a controlled pH to produce a fermentate. The hydrolytic enzyme may be a cellulase, a hemicellulase, a glucanase, a xylanase, or an amylase. The fruit or vegetable extract may be onion extract, sweet potato extract, celery extract, carrot extract, chick pea extract, tomato extract, spinach extract or apple extract. The fermenting microorganism may be a *Lactococcus* species, a *Lactobacillus* species, a *Streptococcus* species, a *Pediococcus* species, a *Propionibacterium* species, or any combination thereof. In certain embodiments, the fermenting microorganism is *Lactococcus lactis, Lactobacillus acidophilus, Lactobacillus plantarum, Lactobacillus reuteri, Propionibacterium freudenreichii, Propionibacterium acidipropionici, Lactobacillus brevis, Lactobacillus sakei, Pediococcus acidilactici*, or any combination thereof. The fermentate may include a cellular mass component with at least one metabolite that is lactic acid, lactate, propionic acid, acetic acid, ethanol, or any combination thereof. The controlled temperature is between about 10° C. and about 50° C., and the controlled pH is between about 3 and about 10; however such ranges may be further refined as described herein. The fermentate has the ability to inhibit the growth of a contaminating microorganism by 100% when diluted to less than 5% (w/v).

The method for producing a fermentate may further include a step of evaporating the fermentate to produce a second fermentate. The method may also include a step of spray-drying the second fermentate to produce a powdered fermentate. Alternatively or conjunctively, the method may include a step of clarifying the fruit or vegetable extract. In certain embodiments, the fruit or vegetable extract is clarified prior to the step of mixing the fruit or vegetable extract with a fermenting microorganism, water, and a growth media. The step of mixing may further include mixing with a fermented yeast extract.

Food Products

In a further aspect of the present invention, food products are provided. The food products may include anyone of the fermentates disclosed herein or any one of the fermentates made by the methods disclosed herein. Surprisingly, as reported in the non-limiting Examples, the present inventors demonstrate that fermentates produced using fruit or vegetable extracts as a substrate displayed significant antimicrobial activity against various microorganisms.

As used herein, a "food product" may include any food product susceptible to microbial contamination or degradation. In some embodiments, the food product may be any food product that has a water activity greater than 0.2, 0.3, 0.35, 0.4, 0.45, 0.5, 0.55, 0.6, 0.65, 0.7, 0.75, 0.8, 0.85, or 0.9. Suitable food products may include, without limitation, culinary items, bakery items, cereals, pasta, meats, dairy items, rice, fish, nuts, beverages, confections, pet food, fruits, and vegetables.

Bakery items may include, without limitation, Breads, buns, rolls, Quick breads (biscuits, muffins, tortillas, cornbread, etc.), Sweet goods (cakes, brownies, cookies, pies, etc.), or Bakery Fillings (dairy-based, fruit-based, etc.).

Meats may include, without limitation, Cured Meats, Raw Beef/Pork (ground meat, whole muscle, etc.), Raw Poultry (ground poultry, whole muscle, etc.), Fermented meats, Emulsified meats (hot dogs, etc.), or Dried Meats.

Culinary items may include, without limitation, Dressings, Condiments, Mayonnaise, Sauces and gravies, Soups, Ready to eat dips, salsa, spreads, Ready to eat side items (coleslaw, potato salad, chicken salad, etc.), Ready to eat meals (lasagna, casserole, pasta dishes, etc.), jams, jellies, marmalades, fruit fillings, Desserts and puddings, or Syrups.

Beverages may include, without limitation, Teas, Coffee and coffee-based drinks, Fruit and vegetable juices, Fermented beverages, Beverage concentrates, Soft drinks, Acidified milk drinks and milk-based beverages, Carbonated soft drinks, Drink mixers (base used for bloody Mary's, margaritas, cocktails, etc.), Beer, or Wine.

Confections may include, without limitation, Chocolate and chocolate-based confections, Cakes, cookies, and other sweet treats.

Dairy items may include, without limitation, Fresh fermented dairy (cottage cheese, cream cheese, etc.), Dairy-based drinks (yogurt drinks, high-protein dairy drinks, etc.), Flavored milks, Cheese (shredded cheese, cheese blocks, etc.), Whipped toppings, Dairy-based desserts (flan, custard, pudding, etc.), Dairy-based dips (sour cream-based, Greek yogurt-based, etc.), Butter and spreads.

Pet food may include, without limitation, Kibble, Low- and high-moisture treats, Refrigerated rolls (meat rolls, veggie rolls, etc.), Palatants and flavor-enhancers, Broths, or Jerky.

In some embodiments, the food product may have a pH between about 1 and about 14, about 1 and about 10, about 1 and about 9, about 3 and about 8, or about 4 and about 8.

Additionally, the present application contemplates a food product including a fermentate having a cellular mass component from a fermenting microorganism, a fermented fruit or vegetable extract and a hydrolytic enzyme. The food product may have a pH between about 3 and about 10, preferably between 3 and 8, or at any sub-range between 3 and 10. In certain embodiments, the food product has a water activity greater than 0.6. The food product may be culinary items, bakery items, cereals, pasta, meats, dairy items, rice, fish, nuts, beverages, confections, pet food, fruits, or vegetables. In certain embodiments, the food product has a volume and includes the fermentate in a concentration between about 0.1% and about 5% of the food product volume, or at any range therein as described elsewhere in this application. The fermentate of the food product may be a concentrated liquid or a dry powder, and preferably has the ability to inhibit the growth of a contaminating microorganism by 100% when diluted to less than 5% (w/v).

The fermenting microorganism for the food product may be a *Lactococcus* species, a *Lactobacillus* species, a *Streptococcus* species, a *Pediococcus* species, a *Propionibacterium* species, or a combination thereof. In certain embodiments, the fermenting microorganism may be *Lactococcus lactis, Lactobacillus acidophilus, Lactobacillus plantarum, Lactobacillus reuteri, Lactobacillus brevis, Lactobacillus sakei, Pediococcus acidilactici, Propionibacterium freudenreichii, Propionibacterium acidipropionici*, or combination thereof. The fermented fruit or vegetable extract used may be fermented onion extract, fermented sweet potato extract, fermented celery extract, fermented carrot extract, fermented chick pea extract, or fermented apple extract. The hydrolytic enzyme may be a cellulase, a hemicellulase, a glucanase, a xylanase, or an amylase. The cellular mass component may be lactic acid, lactate, propionic acid, acetic acid, or ethanol. In certain embodiments, the fermentate includes a fermented yeast extract.

Methods for Killing or Inhibiting the Growth of a Microorganism on or within a Food Product In a still further aspect, methods for killing or inhibiting the growth of a contaminating microorganism on or within a food product are provided. The food product has a volume, and the method contemplates the steps of making or obtaining a fermentate comprising a cellular mass component from a fermenting microorganism, a fermented fruit or vegetable extract and a hydrolytic enzyme; and applying an effective amount of the fermentate to the food product so as to kill or inhibit the growth of the contaminating microorganism on or within the food product. The fermentate is preferably applied in a concentration between about 0.08% and about 10% of the food product volume, but any value within that range may be selected, and any sub-range may be applicable as well. For example, the concentration may be between about 0.1 and about 5%, between about 0.2% and about 5%, between about 0.3% and about 5%, between about 0.6% and about 5%, between about 0.6% and about 2.5%, between about 1.25% and about 5%, and between about 1.25% and about 2.5%. The fermentate may be a concentrated liquid or a dry powder and has the ability to inhibit the growth of a contaminating microorganism by 100% when diluted to less than 5% (w/v).

The food product used in the method may be selected from the group consisting of culinary items, bakery items, cereals, pasta, meats, dairy items, rice, fish, nuts, beverages, confections, pet food, fruits, and vegetables. The contaminating microorganism may be a yeast species, a mold species, gram positive bacteria, or gram negative bacteria. In certain embodiments, the contaminating microorganism is a *Rhodotorula* species, a *Saccharomyces* species, *Zygosaccharomyces* species, a *Candida* species, an *Aspergillus* species, a *Penicillium* species, a *Botrytis* species, a *Leuconostoc* species, a *Lactococcus* species, a *Micrococcus* species, a *Lactobacillus* species, or a *Pediococcus* species.

The fermenting microorganism used in the method may be a *Lactococcus* species, a *Lactobacillus* species, a *Streptococcus* species, a *Pediococcus* species, a *Propionibacterium* species, or any combination thereof. In certain embodiments, the fermenting microorganism is *Lactococcus lactis, Lactobacillus acidophilus, Lactobacillus plantarum, Lactobacillus reuteri, Lactobacillus brevis, Lactobacillus sakei, Pediococcus acidilactici, Propionibacterium freudenreichii, Propionibacterium acidipropionici*, or any combination thereof. The fermented fruit or vegetable extract used in the method may be fermented onion extract, fermented sweet potato extract, fermented celery extract, fermented carrot extract, fermented chick pea extract, or fermented apple extract. The hydrolytic enzyme used in the method may be a cellulase, a hemicellulase, a glucanase, a xylanase, or an amylase. The cellular mass component may include at least one metabolite that is lactic acid, lactate, propionic acid, acetic acid, ethanol, or any combination thereof. In certain embodiments, the method contemplates that the fermentate further comprises making or obtaining a fermentate including a fermented yeast extract.

"Effective amount" is intended to mean an amount of a fermentate described herein sufficient to inhibit the growth of a contaminating microorganism on a food product by, for example, 10%, 20%, 50%, 75%, 80%, 90%, 95%, or 1-fold, 3-fold, 5-fold, 10-fold, 20-fold, or more compared to a negative control. In some embodiments, the effective amount of a fermentate may be between about 0.1% and about 10% or any range therein. A "negative control" refers to a sample that serves as a reference for comparison to a test sample. For example, a test sample can be taken from a test condition including the presence of a fermentate and compared to negative control samples lacking the fermentate. One of skill in the art will recognize that controls can be designed for assessment of any number of parameters.

ILLUSTRATIVE EMBODIMENTS

Embodiment 1: a fermentate comprising a cellular mass component from a fermenting microorganism and a fermented fruit or vegetable extract.

Embodiment 2: the fermentate of embodiment 1, further comprising a fermented yeast extract.

Embodiment 3: the fermentate of any one of the preceding embodiments, further comprising a hydrolytic enzyme.

Embodiment 4: the fermentate of embodiment 3, wherein the hydrolytic enzyme is selected from the group consisting of a cellulase, a hemicellulase, a glucanase, a xylanase, and an amylase.

Embodiment 5: the fermentate of any one of the preceding embodiments, wherein the cellular mass component comprises at least one metabolite selected from the group consisting of lactic acid, lactate, propionic acid, acetic acid, and ethanol.

Embodiment 6: the fermentate of any one of the preceding embodiments, wherein the fermented fruit or vegetable extract is selected from the group consisting of fermented onion extract, fermented sweet potato extract, fermented celery extract, fermented carrot extract, fermented chick pea extract, and fermented apple extract.

Embodiment 7: the fermentate of any one of the preceding embodiments, wherein the fermenting microorganism is selected from the group consisting of a *Lactococcus* species, a *Lactobacillus* species, a *Streptococcus* species, a *Pediococcus* species, a *Propionibacterium* species, and combinations thereof.

Embodiment 8: the fermentate of any one of the preceding embodiments, wherein the fermenting microorganism is selected from the group consisting of *Lactococcus lactis, Lactobacillus acidophilus, Lactobacillus plantarum, Lactobacillus reuteri, Lactobacillus brevis, Lactobacillus sakei, Pediococcus acidilactici, Propionibacterium freudenreichii, Propionibacterium acidipropionici*, and combination thereof.

Embodiment 9: the fermentate of any one of the preceding embodiments, wherein the fermentate has the ability to inhibit the growth of a contaminating microorganism by 100% when diluted to less than 5% (w/v).

Embodiment 10: the fermentate of any one of the preceding embodiments, wherein the fermentate is a concentrated liquid.

Embodiment 11: the fermentate of any one of the preceding embodiments, wherein the fermentate is a dry powder.

Embodiment 12: A Method for Producing a Fermentate Comprising:
(a) obtaining a fruit or vegetable extract,
(b) mixing the fruit or vegetable extract with a fermenting microorganism, water, and a growth media capable of supporting the growth of the fermenting microorganism to produce a liquid composition, and
(c) incubating the liquid composition at a controlled temperature and a controlled pH to produce a fermentate.

Embodiment 13: the method of embodiment 12, further comprising evaporating the fermentate to produce a second fermentate.

Embodiment 14: the method of embodiment 13, further comprising spray-drying the second fermentate to produce a powdered fermentate.

Embodiment 15: the method of any one of embodiments 12-14, further comprising treating the fruit or vegetable extract with a hydrolytic enzyme.

Embodiment 16: the method of embodiment 15, wherein the fruit or vegetable extract is treated with a hydrolytic enzyme prior to step (b).

Embodiment 17: the method of any one of embodiments 15-16, wherein the hydrolytic enzyme is selected from the group consisting of a cellulase, a hemicellulase, a glucanase, a xylanase, and an amylase.

Embodiment 18: the method of any one of embodiments 12-17, further comprising clarifying the fruit or vegetable extract.

Embodiment 19: the method of embodiment 18, wherein the fruit or vegetable extract is clarified prior to step (b).

Embodiment 20: the method of any one of embodiments 12-19, wherein the fruit or vegetable extract is selected from the group consisting of onion extract, sweet potato extract, celery extract, carrot extract, chick pea extract, tomato extract, spinach extract and apple extract.

Embodiment 21: the method of any one of embodiments 12-20, wherein the fermenting microorganism is selected from the group consisting of a *Lactococcus* species, a *Lactobacillus* species, a *Streptococcus* species, a *Pediococcus* species, a *Propionibacterium* species, and combinations thereof.

Embodiment 22: the method of embodiment 21, wherein the fermenting microorganism is selected from the group consisting of *Lactococcus lactis, Lactobacillus acidophilus, Lactobacillus plantarum, Lactobacillus reuteri, Propionibacterium freudenreichii, Propionibacterium acidipropionici, Lactobacillus brevis, Lactobacillus sakei, Pediococcus acidilactici*, and combinations thereof.

Embodiment 23: the method of any one of embodiments 12-22, wherein the controlled temperature is between about 10° C. and about 50° C.

Embodiment 24: The Method of any One of Embodiments 12-23, Wherein the Controlled pH is Between about 3 and about 10.

Embodiment 25: a food product comprising any one of the fermentates of embodiments 1-11 or any one of the fermentates made by the methods of embodiments 12-24.

Embodiment 26: the food product of embodiment 25, wherein the food product has a pH between about 3 and about 8.

Embodiment 27: the food product of any one of embodiments 25-26, wherein the food product has a water activity greater than 0.6.

Embodiment 28: the food product of any one of embodiments 25-27, wherein the food product is selected from the group consisting of culinary items, bakery items, cereals, pasta, meats, dairy items, rice, fish, nuts, beverages, confections, pet food, fruits, and vegetables.

Embodiment 29: A Method for Killing or Inhibiting the Growth of a Contaminating Microorganism on or within a Food Product Comprising:
  making or obtaining any one of the fermentates of embodiments 1-11 or performing any one of the methods of embodiments 12-24; and
  applying an effective amount of the fermentate to the food product so as to kill or inhibit the growth of the contaminating microorganism on or within the food product.

Embodiment 30: the method of embodiment 29, wherein the fermentate is applied in an amount between about 0.1% and about 5%.

Embodiment 31: the method of any one of embodiments 29-30, wherein the contaminating microorganism is selected from the group consisting of a yeast species, a mold species, a gram positive bacteria, and a gram negative bacteria.

Embodiment 32: the method of embodiment 31, wherein the contaminating microorganism is selected from the group consisting of a *Rhodotorula* species, a *Saccharomyces* species, *Zygosaccharomyces* species, a *Candida* species, an *Aspergillus* species, a *Penicillium* species, a *Botrytis* species, a *Leuconostoc* species, a *Lactococcus* species, a *Micrococcus* species, a *Lactobacillus* species, and a *Pediococcus* species.

Embodiment 33: the method of any one of embodiments 29-32, wherein the food product is selected from the group consisting of culinary items, bakery items, cereals, pasta, meats, dairy items, rice, fish, nuts, beverages, confections, pet food, fruits, and vegetables.

Embodiment 34: A Fermentate Produced by any One of the Methods of Embodiments 12-24.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1 mM to 50 mM, it is intended that values such as 2 mM to 40 mM, 10 mM to 30 mM, or 1 mM to 3 mM, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1: General Methods

This section describes the general strains, enzymes, and methods used in the following examples unless changes are otherwise noted.

TABLE 1

| Species list | |
| --- | --- |
| Genus | Spp |
| *Lactococcus* | *lactis* |
| *Lactobacillus* | *plantarum* |

TABLE 2

List of enzymes used in these experiments.
All enzymes are commercially available,
food grade, non-gmo enzymes

| Enzyme | Vendor |
| --- | --- |
| Bacterial Amylase L | Bio-Cat |

TABLE 2-continued

List of enzymes used in these experiments.
All enzymes are commercially available,
food grade, non-gmo enzymes

| Enzyme | Vendor |
| --- | --- |
| Cellulase 2XL | Bio-Cat |
| Hemicellulase | Bio-Cat |

Standard Shake Flask Method:

Single bacterial colonies were picked into 10 milliliters (ml) of appropriate growth media and grown for ~24 hours (hrs) at 37° C. An aseptic 1% volumetric transfer was made from the overnight culture to an individual 250 ml Erlenmyer flask sterilized with 100 ml of the appropriate media components including 1% $CaCO_3$ (buffer) and yeast extract, and cooled to room temperature (~22° C.). The inoculated flasks were incubated in a 32° C. shaking (150 rpm) incubator and grown for 20-24 hours. Following fermentation, the cultures were enumerated to determined CFU/ml (colony forming units/ml) using standard media and methods. A portion of the fermentation growth was filter-sterilized and tested for activity using a well diffusion assay to determine the level of antimicrobial production (method described below).

Well Diffusion Assay:

A single Micrococcus luteus colony was picked from an agar plate and transferred into 10 ml of Trypticase Soy Broth (TSB) and incubated overnight with shaking (~150 rpm) at 32° C. After 20-24 hrs a sterile 1% transfer was made into tempered Trypticase Soy Agar and 17 ml was added to sterile petri plates and allowed to solidify. Once plates solidified, the back end of a sterile 5 ml serological pipette was used to remove six agar plugs equidistant from each other in a circular pattern. The plugs were filled with 20 μl of tempered sterile agar to seal them and form wells. The wells were filled with 40 μl of filter-sterilized test material which was prepared as follows. Briefly, 10 ml of fermentation broth was transferred to a 15 ml conical tube and centrifuged for 10 min at 4700 rpm. The resulting supernatant was filter-sterilized with a 0.22 μm filter unit and stored at 4° C. until use or kept at −20° C. for longer term storage. When noted, the test materials were diluted with sterile 0.1% peptone to the appropriate dilution prior to addition to the wells. After wells were filled with test material the plates were incubated agar-side down at 32° C. for 24 hours. Activity was recorded by measuring the diameter (mm) of the zone of inhibition formed around each well using digital calipers.

Enzyme Treatments:

Standard enzyme treatment involved adding the test substrate to sterile water and adding the appropriate amount of enzyme based on the final volume of solution. The flasks were incubated in a water bath set at 50-60° C. and swirled flasks every 15 min for 60 minutes.

Example 2: Production of Antimicrobial Fermentates Using Vegetable Extracts

To determine if it was possible to produce antimicrobial substances using strictly vegetable powders, Lactococcus lactis, was grown in 5% rehydrated sweet potato powder and compared to the same culture grown in 5% dextrose. In addition, both flasks contained 2% yeast extract and buffer. Results of enumeration of growth and activity against M. luteus are summarized in Table 3.

TABLE 3A

Growth and Activity Against M. luteus
from Dextrose and Sweet Potato Fermentates

| | | | Well Diffusion Assay Zone of Inhibition (mm) | | |
| --- | --- | --- | --- | --- | --- |
| Substrate | Concentration | CFU/ml | 50% | 25% | 12.5% |
| Dextrose | 5% | 2.46E+09 | 14.46 | 10.2 | 9.075 |
| Cultured Sweet potato | 5% | 1.45E+09 | 12.85 | 9.13 | 7.93 |

This test demonstrated that it was possible to grow L. lactis strain 10528 on a vegetable powder, as the cell counts in both substrates were similar. The inventors were also able to achieve a significant level of antimicrobial metabolite activity, based on the inhibition of M. luteus as shown in the well diffusion assay.

It is known that some vegetables and spices (e.g. onion) have antimicrobial effects without culturing. Accordingly, a study was made to determine if uncultured onion powder and chickpea flour have any antimicrobial effects against the indicator test organism, Micrococcus luteus. A 10% solution of onion powder and 10% solution of chickpea flour were prepared in sterile water, allowed to rehydrate for 15 minutes at room temperature, then centrifuged, and the resulting supernatants were filtered. A 10% sample of a commercial cultured dextrose product was also prepared in the same manner to be used as an internal benchmark control. All samples were tested in duplicate against M. luteus in a well diffusion assay as explained previously. Table 3B demonstrates that there were no zones of inhibition present in either of the uncultured onion or chickpea samples, however, the cultured dextrose control did produce zones of inhibition.

TABLE 3B

Comparison of antimicrobial activity of uncultured onion powder
and chickpea flour to a commercial cultured dextrose product

| | Zone of Inhibition (mm) | | | | | |
| --- | --- | --- | --- | --- | --- | --- |
| | 10% | 5% | 2.5% | 1.25% | 0.63% | 0.31% |
| Uncultured Onion | 0 | 0 | 0 | 0 | 0 | 0 |
| Uncultured Chickpea | 0 | 0 | 0 | 0 | 0 | 0 |
| Cultured Dextrose | 19.84 | 17.23 | 15.16 | 12.38 | 10.61 | 0 |

Example 3: Production of Non-antimicrobial Fermentates Using Vegetable Extracts The inventors also investigated whether or not it was possible to achieve similar growth with non-antimicrobial producing strains using alternative substrates. Three different lactic acid bacteria strains were tested that could potentially be used to develop fermented flavor products or for other applications where growth on vegetable or other substrates could be beneficial, but antimicrobial activity isn't required or desired. Since the strains used are not known to be antimicrobial, the well diffusion assay was not tested. The flasks did not contain $CaCO_3$. Yeast extract was added to each of the fermentations. A summary of the work is listed in Table 4.

TABLE 4

Fermentation of Carrot Powder using non-antimicrobial
L. lactis and L. plantarum strains

| Flask | Carrot Powder | Yeast Extract | Dextrose | Cell Count |
|---|---|---|---|---|
| 1-L.lactis strain A | 5% | — | — | 3.10E+08 |
| 2-L.lactis strainA | 5% | — | 1% | >10^9 |
| 3-L.lactis strain A | 5% | 0.5% | 1% | 9.20E+05 |
| 4-L. plantarum strain B | 5% | — | — | >10^9 |
| 5-L. plantarum strain B | 5% | — | 1% | 5.00E+08 |
| 6-L. plantarum strain B | 5% | 0.5% | 1% | >10^9 |
| 7-L. plantarum strainC | 5% | — | — | >10^9 |
| 8-L. plantarum strain C | 5% | — | 1% | >10^9 |
| 9-L. plantarum strain C | 5% | 0.5% | 1% | >10^9 |

These experiments demonstrated that simply using vegetable powder alone can produce a similar level of bacterial growth when compared to growth from using Dextrose and/or yeast extract for both three different L. lactis or L. plantarum strains.

Example 4: Pretreatment of Fruit or Vegetable Extracts with Hydrolytic Enzymes

Although the fruit and vegetables powders did contain some free sugars, it was surmised that much of the sugar is bound in the form of complex carbohydrates, including cell wall material and starch. To investigate, the inventors conducted several studies utilizing various hydrolytic enzymes to increase the amount of available sugars for fermentation. All of the following studies used L. lactis as the fermentation culture.

Carrot: The total carbohydrates in the carrot powder were almost entirely fiber (81% out of 81.9% total carbs), therefore, the inventors chose to digest this substrate with a cellulase and/or hemi-cellulase. The results, summarized in table 5 demonstrate that when no enzyme was used there was no antimicrobial activity present. However, the addition of cellulase either alone or in combination with hemi-cellulase resulted in antimicrobial activity in all but one test. The inventors also showed that by lowering the concentration of carrot powder activity is still present when used with an enzyme treatment. Also included on this table is a column that estimates, based on substrate nutritional information, the estimated amount of "sugar" that is present before liberation of any sugars using the enzyme treatment and is based on nutritional data provided from the supplier and not on any analytical measure that was performed.

TABLE 5

Utilization of hydrolytic enzymes on carrot powder

| Substrate | Conc | Estimated sugar | Hemi-cellulase | Cellulase | CFU/ml | Zone of Inhibition (mm) 50% | 25% |
|---|---|---|---|---|---|---|---|
| Dextrose | 5.0% | 5% | — | — | 3.00E+09 | 15.5 | 13 |
| Carrot | 3.0% | 0.039% | — | — | 5.35E+08 | 0.0 | 0.0 |
| Carrot | 3.0% | 0.039% | — | 0.05% | 4.15E+08 | 8.1 | 0.0 |
| Carrot | 3.0% | 0.039% | — | 0.075% | 5.15E+08 | 8.2 | 0.0 |
| Carrot | 3.0% | 0.039% | — | 0.10% | 7.65E+08 | 8.7 | 0.0 |
| Carrot | 3.0% | 0.039% | 0.10% | 0.05% | 1.30E+08 | 8.3 | 0.0 |
| Carrot | 2.0% | 0.026% | — | 0.10% | 5.55E+08 | 8.3 | 0.0 |

Celery Juice: Similar to the carrot powder, celery juice (liquid) was tested along with celery juice (powder) with and without cellulase. In the liquid substrate, the enzyme treatment resulted in more activity then without the enzyme treatment (Table 6).

TABLE 6

Cellulase treatment of celery juice and juice powder

| Substrate | Conc. | Estimated sugar | Cellulase | CFU/ml | Zone of Inhibition (mm) 50% | 25% | 12.5% |
|---|---|---|---|---|---|---|---|
| Celery Juice | 16% | 2.9% | — | 1.70E+09 | 9.50 | 7.40 | — |
| Celery Juice | 16% | 2.9% | 0.075% | 7.15E+09 | 13.20 | 11.20 | — |

The celery powder was tested using various enzyme combinations. Cellulase was tested, with and without amylase as well as amylase alone. Activity was highest in the cellulase treated sample without the addition of amylase compared to no enzyme treatment (Table 7).

TABLE 7

Second test confirming the advantage of using cellulase with celery powder
for optimal antimicrobial production

| Substrate | Conc. | Estimated sugar | Cellulase | Amylase | CFU/ml | Zone of Inhibition (mm) 50% | 25% | 12.5% |
|---|---|---|---|---|---|---|---|---|
| Celery powder | 5% | 0.6% | — | — | 2.35E+09 | 13.84 | 11.34 | 9.34 |
| Celery powder | 5% | 0.6% | 0.075% | 0.75% | 4.05E+09 | 12.75 | 10.52 | 9.8 |
| Celery powder | 5% | 0.6% | — | 0.75% | 4.20E+09 | 13.30 | 11.86 | 9.65 |
| Celery powder | 5% | 0.6% | 0.075% | — | 2.45E+09 | 14.40 | 12.88 | 10.26 |

Sweet Potato: Sweet potato powder was tested with cellulase with and without amylase. Based on the nutritional information roughly half of the carbohydrates were not fiber or sugar (it is presumed that the majority of the remaining carbohydrates were from starch). The use of cellulase combined with amylase made a distinct improvement in antimicrobial activity and cell count when compared to cellulase alone or no enzyme (Table 8).

TABLE 8

Comparison of fermentation of potato powder treated with enzyme or no enzyme

| Substrate | Conc. | Estimated sugar | Cellulase | Amylase | CFU/ml | Zone of Inhibition (mm) | | |
|---|---|---|---|---|---|---|---|---|
| | | | | | | 50% | 25% | 12.5% |
| Sweet potato | 5% | 1.0% | — | — | 1.75E+08 | 9.33 | 0.00 | 0.00 |
| Sweet potato | 5% | 1.0% | 0.075% | — | 3.65E+08 | 10.32 | 8.30 | 0.00 |
| Sweet potato | 5% | 1.0% | 0.075% | 0.75% | 5.54E+08 | 12.81 | 11.06 | 8.91 |

Apple Fiber: Apple fiber powder with and without cellulase enzyme treatment were tested. The cellulase treated sample only performed slightly better than not using enzymes.

TABLE 9

Comparison of the fermentation of apple fiber powder with and without cellulase

| Substrate | Conc. | Estimated sugar | Cellulase | CFU/ml | Zone of Inhibition (mm) | | |
|---|---|---|---|---|---|---|---|
| | | | | | 50% | 25% | 12.5% |
| Apple Powder | 5% | 1.6% | — | 2.60E+09 | 12.17 | 10.66 | 9.04 |
| Apple Powder | 5% | 1.6% | 0.075% | 3.65E+09 | 12.41 | 10.58 | 9.88 |

Chick Pea Flour: Similar to the sweet potato powder, a sample of chick pea flour which was high in starch content was tested with an amylase enzyme. The addition of amylase made a distinct improvement in antimicrobial activity (Table 10).

TABLE 10

Effect of amylase treatment on antimicrobial activity

| Substrate | Conc. | Estimated sugar | Amylase | Cell Count | Zone of Inhibition (mm) | | |
|---|---|---|---|---|---|---|---|
| | | | | | 50% | 25% | 12.5% |
| Chick Pea Flour | 5% | 0.119% | — | 1.00E+09 | 9.49 | 7.95 | 0 |
| Chick Pea Flour | 5% | 0.119% | 0.75% | 1.70E+09 | 13.40 | 10.53 | 8.75 |

Onion Powder: Onion Powder was tested with and without the addition of cellulase treatment. The activity increased with the addition of the enzyme treatment (Table 11).

TABLE 11

Onion powder when fermented with and without cellulose

| | | Estimated | | | Zone of Inhibition (mm) | | |
|---|---|---|---|---|---|---|---|
| Substrate | Conc. | sugar | Cellulase | CFU/ml | 50% | 25% | 12.5% |
| Onion Powder | 5% | 0.330% | — | 1.85E+09 | 12.53 | 9.81 | 8.56 |
| Onion Powder | 5% | 0.330% | 0.075% | 2.00E+09 | 13.14 | 10.90 | 9.41 |

Example 5: Clarification of Fruit or Vegetable Extracts

It was noted that activity seemed to increase when the solids were removed. In this example, centrifugation after enzyme treatment was utilized to remove most of the solids. Other methods, including but not limited to filtration or other methods of removal of large solids could also have been used. The resulting "clarified" growth media was then sterilized and combined with sterilized yeast extract prior to inoculation of the fermentation culture.

In this example, two 1 L flasks each with 250 ml of 5% sweet potato powder were utilized. One of the flasks incorporated an amylase treatment and the other did not. After the enzyme treatment, 100 ml from each flask was clarified via centrifugation. The resulting broth from the clarified samples as well as 100 ml of unclarified broth was sterilized, combined with sterile yeast extract, and inoculated with the fermentation culture. The results indicate that the addition of amylase treatment or clarification increased activity, however, a treatment employing both amylase and solids removal provided the highest activity (Table 12).

Example 6: The Antimicrobial Activity of Spray Dried Fermentation of *Lactococcus lactis* Grown on Sweet Potato Powder and Apple Fiber Powder A study was made to determine the antimicrobial activity of spray dried fermentation of *Lactococcus lactis* when fermented on sweet potato powder and apple fiber powder in shake flasks. A 500 ml Erlenmeyer flask was prepared with 200 ml of either 5% clarified sweet potato powder (treated with 0.75% Amylase L for 1 hour) or 5% clarified apple powder (treated with 0.075% cellulase for 1 hour). Both flasks received 1% yeast extract and buffer. After sterilization, the flasks were inoculated with 1% *L. lactis* previously grown for 20-24 hours in MRS broth. Flasks were incubated at 32° C. shaking at 125 rpm. The shake flasks were stopped at 18 hours at which time the fermentation material was spray dried using a benchtop spray dryer. A 5% solution of spray dried material was prepared in sterile water, allowed to rehydrate for 15 minutes at room temperature, then centrifuged, and the resulting supernatant was filtered. The two filtered spray dried samples were tested in duplicate against *Micrococcus luteus* in a well diffusion assay and compared to a sample of dried commercial cultured dextrose product produced by the same *L. lactis* strain as an internal benchmark control. As shown in Table 13, the spray dried fermentation of *L. lactis* grown on sweet potato powder and apple fiber powder both produced zones of inhibition against *M. luteus* that were greater than those produced by the cultured dextrose product of the same strain.

TABLE 12

Advantage of clarifying enzymatic broth prior to fermentation

| | | Estimated | | | Zone of Inhibition (mm) | | |
|---|---|---|---|---|---|---|---|
| Substrate | Conc. | Sugar | Amylase | | CFU/ml | 50% | 25% | 12.50% |
| Sweet potato | 5% | 1.0% | — | | 1.25E+09 | 11.60 | 10.17 | 8.7 |
| Sweet potato | 5% | 1.0% | — | Clarified | 2.00E+08 | 13.50 | 11.76 | 9.6 |
| Sweet potato | 5% | 1.0% | 0.75% | | 2.40E+08 | 13.75 | 11.86 | 10.04 |
| Sweet potato | 5% | 1.0% | 0.75% | Clarified | 1.16E+09 | 15.60 | 13.72 | 11.45 |

TABLE 13

Comparison of antimicrobial activity of *Lactococcus lactis* fermented on sweet potato powder and apple fiber powder to a commercial cultured dextrose product of the same strain.

| | Zone of Inhibition (mm) | | | | | |
|---|---|---|---|---|---|---|
| | 2.50% | 1.25% | 0.63% | 0.31% | 0.16% | 0.08% |
| Sweet Potato | 29.05 | 26.43 | 23.85 | 21.75 | 19.70 | 17.81 |
| Apple Fiber | 28.71 | 27.18 | 23.76 | 21.44 | 19.16 | 16.84 |
| Cultured Dextrose | 25.53 | 23.87 | 21.31 | 19.35 | 17.22 | 13.60 |

Example 7: *Lactobacillus reuteri* can Produce Greater Antimicrobial Activity when Fermented on Sweet Potato Flour with Enzymatic Treatment A shake flask study was conducted to determine the ability of *Lactobacillus reuteri* to produce antimicrobial activity when fermented on sweet potato flour with and without enzymatic treatment. Shake flasks contained either 4% sweet potato flour treated with 0.75% Amylase L for 1 hour then clarified or 4% sweet potato processed under the same conditions as the treated flask but without the enzyme treatment. Both flasks also received a solution of yeast extract, glycerol and buffer. Flasks were inoculated with 1% *L. reuteri*, previously grown for 6-8 hours in MRS broth. Flasks were incubated anaerobically at 32° C., shaking 125 rpm, for 48 hours. A 5 ml sample was removed from each flask after 24, 40, and 48 hours for pH analysis then the samples were centrifuged, and the resulting supernatants were filtered. As shown in Table 14, the pH of the *L. reuteri* grown on sweet potato with and without enzyme treatment was similar at all time points and the drop in pH indicates growth of the organism due to the buildup of lactic acid in the media.

TABLE 14 pH of *Lactobacillus reuteri* grown on sweet potato with (+) and without (−) enzyme treatment over time.

| | pH of flasks | | | |
|---|---|---|---|---|
| | Initial | 24 hr | 40 hr | 48 hr |
| 4% (+) | 6.74 | 3.96 | 3.72 | 3.67 |
| 4% (−) | 6.77 | 4.03 | 3.80 | 3.76 |

The filtered samples were then tested against *Saccharomyces cerevisae*, strain Y-1545, obtained by the ARS NRRL culture collection, using a serial dilution assay. Strain Y-1545 was grown in Potato Dextrose Broth (PDB) at 32° C. for 24 hours then diluted to a 0.5 McFarland in PDB. The assay was set up in a 96-well low-profile clear assay plate with wells in row "A" containing 180 µl PDB and wells in rows "B" through "G" containing 100 µl PDB. A 20 µl volume of the filtered test sample was added to duplicate wells in row "A" and mixed gently with a pipette, resulting in a test concentration of 10%. Extra wells in row "A" were used for positive and negative controls which were inoculated with 20 µl of sterile water. Serial dilutions were made by transferring 100 µl from row "A" to row "B," mixed gently, then 100 µl from row "B" transferred to row "C," mixed gently, and so on until 100 µl is added to row "H," mixed gently and then 100 µl removed from row "H" so all wells contained 100 µl total providing the following test concentrations: 10%, 5%, 2.5%, 1.25%, 0.63%, 0.31%, 0.16%, 0.08%. All wells, except for the negative control wells, were inoculated with 2 µl of diluted Y-1545. The assay plate was covered with a clear plate seal and incubated at 32° C. for 16-20 hours. The optical density was measured by first gently mixing all wells with a pipette and then read on a plate reader at 600 nm wavelength. As shown in Table 15, the ability of *L. reuteri* to prevent growth of *S. cerevisae* was greater in the sweet potato fermentations with enzyme treatment compared to the fermentation without enzyme treatment at 40 and 48 hours.

TABLE 15

Optical density (600 nm) of *Saccharomyces cerevisae*, strain Y-1545, grown in the presence of *Lactobacillus reuteri* fermented on Sweet Potato with (+) and without (−) enzyme treatment over time.

| (+) | 24 h | | 40 h | | 48 h | | Pos Control | | Neg Control | |
|---|---|---|---|---|---|---|---|---|---|---|
| 10.0% | 0.495 | 0.463 | 0.042 | 0.042 | 0.043 | 0.042 | 0.458 | 0.458 | 0.041 | 0.041 |
| 5.0% | 0.482 | 0.48 | 0.041 | 0.041 | 0.041 | 0.041 | 0.483 | 0.472 | 0.04 | 0.04 |
| 2.5% | 0.476 | 0.471 | 0.141 | 0.139 | 0.062 | 0.064 | 0.456 | 0.427 | 0.04 | 0.04 |
| 1.25% | 0.46 | 0.44 | 0.382 | 0.371 | 0.291 | 0.296 | 0.459 | 0.454 | 0.04 | 0.04 |
| 0.63% | 0.43 | 0.434 | 0.487 | 0.462 | 0.44 | 0.433 | 0.467 | 0.464 | 0.04 | 0.04 |
| 0.31% | 0.429 | 0.431 | 0.503 | 0.495 | 0.463 | 0.471 | 0.469 | 0.469 | 0.04 | 0.04 |
| 0.16% | 0.399 | 0.408 | 0.514 | 0.513 | 0.489 | 0.491 | 0.476 | 0.477 | 0.041 | 0.04 |
| 0.08% | 0.437 | 0.417 | 0.514 | 0.508 | 0.501 | 0.516 | 0.507 | 0.489 | 0.042 | 0.04 |
| (−) | 24 h | | 40 h | | 48 h | | Pos Control | | Neg Control | |
| 10.0% | 0.543 | 0.535 | 0.247 | 0.236 | 0.044 | 0.044 | 0.427 | 0.402 | 0.042 | 0.04 |
| 5.0% | 0.498 | 0.5 | 0.451 | 0.425 | 0.268 | 0.228 | 0.433 | 0.429 | 0.04 | 0.04 |
| 2.5% | 0.478 | 0.491 | 0.537 | 0.51 | 0.407 | 0.368 | 0.43 | 0.432 | 0.04 | 0.04 |

TABLE 15-continued

Optical density (600 nm) of *Saccharomyces cerevisae*, strain Y-1545, grown in the presence of *Lactobacillus reuteri* fermented on Sweet Potato with (+) and without (−) enzyme treatment over time.

| 1.25% | 0.464 | 0.484 | 0.528 | 0.523 | 0.457 | 0.43  | 0.428 | 0.431 | 0.04  | 0.04 |
| 0.63% | 0.443 | 0.419 | 0.529 | 0.525 | 0.47  | 0.441 | 0.44  | 0.434 | 0.04  | 0.04 |
| 0.31% | 0.424 | 0.462 | 0.562 | 0.5   | 0.461 | 0.472 | 0.44  | 0.449 | 0.04  | 0.04 |
| 0.16% | 0.436 | 0.421 | 0.509 | 0.493 | 0.443 | 0.484 | 0.403 | 0.435 | 0.04  | 0.04 |
| 0.08% | 0.45  | 0.416 | 0.538 | 0.5   | 0.499 | 0.471 | 0.437 | 0.464 | 0.042 | 0.04 |

Example 8: The Antimicrobial Activity of Spray Dried Fermentation of *Propionibacterium freudenreichii* on Sweet Potato Powder A study was conducted to determine the ability of *Propionibacterium freudenreichii* to grow and produce antimicrobial activity when fermented on sweet potato powder in shake flasks and spray dried. A 500 ml Erlenmeyer flask was prepared with 200 ml of either 5% Dextrose or 5% clarified sweet potato powder (treated with 0.75% Amylase L for 1 hour). Both flasks received 1% yeast extract and 0.4% of a buffer. After sterilization, the flasks were inoculated with 1% *P. freudenreichii* previously grown for 24 hours in Sodium Lactate broth. Flasks were incubated anaerobically at 32° C. shaking at 125 rpm. The fermentation was stopped at 116 hours at which time a 3 ml liquid sample was removed from each flask for analysis of pH (Table 16) and enumeration of Propionibacteria, then centrifuged and filtered for analysis of antimicrobial activity. The remaining fermentation material received 5% maltodextrin in each flask and then were spray dried using a benchtop spray dryer. A 10% solution of each spray dried material was prepared in sterile water, allowed to rehydrate for 15 minutes at room temperature, then centrifuged, and the resulting liquids were filtered.

TABLE 16

Analysis of pH and enumeration of Propionibacteria in shake flasks

|              | Initial pH | Final pH | CFU/ml Seed Culture | CFU/ml Final (116 h) |
|---|---|---|---|---|
| Dextrose     | 6.82 | 4.44 | 2.10E+09 | 8.20E+09 |
| Sweet Potato | 6.76 | 4.51 |          | 1.80E+10 |

The filtered liquid and spray dried samples were tested in duplicate against *Candida parapsilosis*, strain Y-619, obtained by the ARS NRRL culture collection, using a serial dilution broth assay. Strain Y-619 was grown in Potato Dextrose Broth (PDB) at 32° C. for 24 hours then diluted to a 0.5 McFarland in PDB. The assay was set up in a 96-well low-profile clear assay plate with wells in rows "A" through "G" containing 100 µl PDB as described in Example 7. All wells, except for the negative control wells, were inoculated with 2 µl of diluted Y-619. The assay plate was covered with a clear plate seal and incubated at 32 C for 16-20 hours. The optical density was measured by first gently mixing all wells with a pipette and then read on a plate reader at 600 nm wavelength. As shown in Tables 17 and 18, the ability of *P. freudenreichii* to prevent the growth of *C. parapsilosis* was similar in the Dextrose and Sweet Potato liquid samples and slightly better in the spray dried Sweet Potato sample compared to Dextrose.

TABLE 17

Optical density (600 nm) of *Candida parapsilosis*, strain Y-619, grown in the presence of liquid *Propionibacterium freudenreichii* fermented on Dextrose or Sweet Potato powder

|       | Liquid Dextrose | | Liquid Sweet Potato | | Positive Control | | Negative Water Control | Negative Dextrose Control | Negative Sweet Potato |
|---|---|---|---|---|---|---|---|---|---|
| 50%   | 0.044 | 0.046 | 0.049 | 0.047 | 0.331 | 0.31  | 0.041 | 0.044 | 0.054 |
| 25%   | 0.058 | 0.062 | 0.059 | 0.058 | 0.339 | 0.336 | 0.041 | 0.042 | 0.046 |
| 12.5% | 0.105 | 0.109 | 0.111 | 0.107 | 0.333 | 0.308 | 0.042 | 0.042 | 0.043 |
| 6.3%  | 0.17  | 0.18  | 0.176 | 0.174 | 0.326 | 0.325 | 0.044 | 0.041 | 0.048 |
| 3.1%  | 0.228 | 0.259 | 0.237 | 0.246 | 0.367 | 0.336 | 0.041 | 0.042 | 0.042 |
| 1.6%  | 0.274 | 0.301 | 0.293 | 0.305 | 0.348 | 0.338 | 0.041 | 0.042 | 0.041 |
| 0.8%  | 0.307 | 0.322 | 0.321 | 0.306 | 0.332 | 0.332 | 0.043 | 0.042 | 0.043 |
| empty | 0.047 | 0.048 | 0.049 | 0.049 | 0.047 | 0.048 | 0.056 | 0.046 | 0.048 |

TABLE 18

Optical density (600 nm) of Candida parapsilosis, strain Y-619, grown in the presence of spray dried Propionibacterium freudenreichii fermented on Dextrose or Sweet Potato powder

| | Spray Dried Dextrose | | Spray Dried Sweet Potato | | Positive Control | | Negative Water Control | Negative Dextrose Control | Negative Sweet Potato |
|---|---|---|---|---|---|---|---|---|---|
| 5% | 0.054 | 0.059 | 0.056 | 0.055 | 0.345 | 0.345 | 0.041 | 0.048 | 0.058 |
| 2.5% | 0.093 | 0.098 | 0.069 | 0.072 | 0.361 | 0.354 | 0.041 | 0.044 | 0.05 |
| 1.3% | 0.153 | 0.176 | 0.125 | 0.131 | 0.357 | 0.376 | 0.041 | 0.042 | 0.045 |
| 0.6% | 0.245 | 0.263 | 0.226 | 0.21 | 0.358 | 0.365 | 0.04 | 0.041 | 0.043 |
| 0.3% | 0.315 | 0.326 | 0.293 | 0.279 | 0.363 | 0.357 | 0.04 | 0.041 | 0.041 |
| 0.2% | 0.336 | 0.344 | 0.334 | 0.323 | 0.368 | 0.36 | 0.04 | 0.041 | 0.043 |
| 0.1% | 0.356 | 0.328 | 0.369 | 0.348 | 0.373 | 0.363 | 0.041 | 0.041 | 0.042 |
| empty | 0.046 | 0.053 | 0.048 | 0.048 | 0.047 | 0.047 | 0.046 | 0.046 | 0.048 |

Example 9: Commercial-Scale Fermentation with Onion Powder

To better model real world conditions, fermented clarified onion powder (5%), was treated with and without cellulase enzyme (0.075%) in 2 L pilot fermentation equipment using *L. lactis* as the fermenting microorganism. Yeast extract (1%) was added to each of the fermentations. The pH was held at 5.5, temperature at 25° C., agitated at 150 RPM and used a 20% CaOH solution base to maintain the proper pH. The fermentation was stopped after 22 hrs. As seen in the previous shake flask examples, the use of cellulase demonstrated a similar level of growth and higher activity at 20 and 22 hours with enzyme treatment when compared to samples that did not use an enzyme (Table 19).

TABLE 19

2L Pilot scale fermentation of onion powder with and without cellulase

| Substrate | Conc. | Total Sugar | Cellulase | CFU/ml 0 h | 20 h | 22 h | Zone of Inhibition (mm) 20 h | 22 h |
|---|---|---|---|---|---|---|---|---|
| Onion Powder | 5% | 0.33% | — | 1.05E+07 | 5.20E+09 | 3.95E+09 | 16.57 | 17.30 |
| Onion Powder | 5% | 0.33% | 0.075% | 1.10E+07 | 4.55E+09 | 3.85E+09 | 18.26 | 18.92 |

Example 10: Dried Powder Applications

Although in some cases liquid fermentation products can be used by customers, the preferred method of delivery is typically in dry powder form. To evaluate the ability to dry fermentates made using vegetable or fruit extracts and maintain antimicrobial activity the following work was conducted.

Experiment 10a—*L. lactis* Production of Antimicrobial Activity on Onion Powder

The 2 L pilot scale fermentation following the method in the previous example (5% onion powder, with cellulase enzyme) was adjusted to pH 4.0 with glacial acetic acid and cooled at the end of fermentation. Approximately 500 ml of this material was then passed through a bench top spray drying system with an inlet temperature of 135° C., aspirator set to 100% and at an inlet pump speed of 30% and the powder was collected. An additional 500 ml of material with the addition of 5% maltodextrin was dried under the same conditions and the powder was collected. The dried powders were diluted and tested in a well diffusion assay as previously described. A sample of dried commercial cultured dextrose product produced by the same *L. lactis* strain was included as an internal benchmark control. The onion powder without maltodextrin showed the highest level of activity (Table 20).

TABLE 20

Comparison of antimicrobial activity of onion powder with and without maltodextrin to a commercial cultured dextrose product of the same strain

| | Zone of Inhibition (mm) | | | | | |
|---|---|---|---|---|---|---|
| | 2.5% | 1.25% | 0.63% | 0.31% | 0.16% | 0.07% |
| Onion Powder | 16.90 | 15.09 | 11.73 | 10.23 | 8.0 | 0 |
| Onion Powder with maltodextrin | 15.11 | 11.89 | 10.22 | 8.75 | 0 | 0 |
| Cultured Dextrose | 14.53 | 12.16 | 10.00 | 8.33 | 0 | 0 |

The experiment was then repeated (5% onion powder, with cellulase enzyme) with the variation that the fermentation was stopped at 20 hours at which time a 10 ml sample of liquid fermentation was removed. The pH was then adjusted to 4.5 using glacial acetic acid and another 10 ml sample liquid fermentation was removed. Both of the liquid samples were centrifuged and the resulting supernatants were filtered. The remaining fermentation received 5% maltodextrin and was then spray dried using a benchtop spray dryer. A 5% solution of spray dried material was prepared in sterile water, allowed to rehydrate for 15 minutes at room temperature, then centrifuged, and the resulting supernatant was filtered. The two filtered liquid samples (pH 5.5 and pH 4.5) were tested in duplicate against *M. luteus* using a well dilution assay as explained previously and to compare the antimicrobial activity before and after addition of acetic acid. The filtered spray dried sample was also tested in duplicate against *M. luteus* in a well diffusion assay and compared to a sample of dried commercial cultured dextrose product produced by the same *L. lactis* strain as an internal benchmark control. Table 21 demonstrates that the pH adjustment of *L. lactis* grown on onion powder did not produce significant differences in the antimicrobial activity against *M. luteus*.

TABLE 21

Comparison of antimicrobial activity of *L. lactis* fermented on onion powder before (pH 5.5) and after (pH 4.5) the pH was adjusted with glacial acetic acid

| | Zone of Inhibition (mm) | | | | | |
|---|---|---|---|---|---|---|
| | 2.5% | 1.25% | 0.63% | 0.31% | 0.16% | 0.07% |
| Onion pH 5.5 | 21.09 | 19.27 | 15.69 | 13.69 | 11.32 | 9.17 |
| Onion pH 4.5 | 21.10 | 19.12 | 16.50 | 13.61 | 11.83 | 9.88 |

Table 22 demonstrates that the spray dried fermentation of *L. lactis* grown on onion powder continued to produce zones of inhibition against *M. luteus* and were greater than those produced by the cultured dextrose product of the same strain.

TABLE 22

Comparison of antimicrobial activity of *L. lactis* fermented on onion powder to a commercial cultured dextrose product of the same strain

| | Zone of Inhibition (mm) | | | | | |
|---|---|---|---|---|---|---|
| | 2.5% | 1.25% | 0.63% | 0.31% | 0.16% | 0.07% |
| Onion Powder | 16.41 | 14.09 | 11.02 | 9.36 | 0 | 0 |
| Cultured Dextrose | 15.61 | 12.85 | 10.56 | 8.69 | 0 | 0 |

Based on the analysis, the level of activity seen by onion powder after spray drying resulted in a commercially viable product for use in numerous applications. In addition, there was no noticeable sensory (taste, smell, visual) issues that stemmed from the drying.

Example 10b: *L. lactis* Production of Antimicrobial Activity on Chickpea Flour

The ability of *L. lactis* to produce antimicrobial activity when fermented on chickpea flour in a 2 L pilot fermentation vessel was examined. A 2 L fermentation vessel with 5% clarified chickpea flour (treated with 0.75% Amylase L for 1 hour), 1% yeast extract and a buffer was prepared. After sterilization, the vessel was held at 25° C. and agitated at 150 rpm for the duration of the fermentation. The vessel was inoculated with 1% *L. lactis* growth, previously grown for 18-24 hours in MRS broth. The pH was allowed to drop naturally until it reached pH 5.5, and then it was held at this pH using Calcium hydroxide for the duration of the fermentation. The fermentation was stopped at 21 hours at which time the pH was adjusted to 4.2 using glacial acetic acid then spray dried using a benchtop spray dryer. A 5% solution of spray dried material was prepared in sterile water, allowed to rehydrate for 15 minutes at room temperature, then centrifuged. The resulting supernatant was filtered and the filtered spray dried sample was tested in duplicate against *M. luteus*, strain B-287, obtained by the ARS NRRL culture collection, using a well dilution assay as explained previously and compared to a sample of dried commercial cultured dextrose product produced by the same *L. lactis* strain as an internal benchmark control. As shown in Table 23, the *L. lactis* grown on chickpea flour produced greater zones of inhibition against *M. luteus* compared to the cultured dextrose product of the same strain.

TABLE 23

Comparison of antimicrobial activity of *L. lactis* fermented on chickpea flour to a commercial cultured dextrose product of the same strain

| | Zone of Inhibition (mm) | | | | | |
|---|---|---|---|---|---|---|
| | 2.5% | 1.25% | 0.63% | 0.31% | 0.16% | 0.07% |
| Chickpea Flour | 17.92 | 14.91 | 11.62 | 9.37 | 8.04 | 0 |
| Cultured Dextrose | 13.25 | 10.33 | 8.8 | 7.6 | 0 | 0 |

Experiment 10c: L. Reuteri Production of Antimicrobial Activity on Chickpea Flour The ability of *L. reuteri* to produce antimicrobial activity when fermented on chickpea flour in a 2 L pilot fermentation vessel was also examined. A 2 L fermentation vessel with 5% clarified chickpea flour (treated with 0.75% Amylase L for 1 hour), 1.5% yeast extract and buffer was prepared. After sterilization, the vessel was held at 30° C., agitated at 100 rpm, and sparged with Nitrogen gas over the headspace for the duration of the fermentation. The vessel was inoculated with 1% *L. reuteri* growth, previously grown for 6-8 hours in MRS broth. The pH was allowed to drop naturally until it reached 4.5, then it was held at this pH using a Calcium hydroxide/glycerol solution for the duration of the fermentation. The fermentation was stopped at 23 hours at which time a 10 ml liquid sample was removed, centrifuged, and the resulting supernatant was filtered. The remaining fermentation was stored at 4° C. for 20-24 hours, then spray dried using a benchtop spray dryer. A 5% solution of spray dried material was prepared in sterile water, allowed to rehydrate for 15 minutes at room temperature, then centrifuged, and the resulting supernatant was filtered.

The filtered liquid and spray dried samples were tested against *Saccharomyces cerevisae*, strain Y-1545, obtained by the ARS NRRL culture collection, using a serial dilution assay. The spray dried sample was diluted 50% in the first well and tested at the following concentrations: 2.5%, 1.25%, 0.63%, 0.31%, 0.16%, 0.08%, 0.04%. Table 24 demonstrates the ability of *L. reuteri* to prevent growth of *S. cerevisae* was >99% at a 2.5% dilution in the liquid fermentation and >99% at a 0.63% dilution in the spray dried fermentation material.

TABLE 24

Optical density (600 nm) of *Saccharomyces cerevisae*, strain Y-1545, grown in the presence of liquid and spray dried fermentation of *Lactobacillus reuteri* on chickpea flour.

| Dilution | Liquid (abs) | | Dilution | Spray Dried (abs) | | Positive Control | | Negative Control | |
|---|---|---|---|---|---|---|---|---|---|
| 10% | 0.042 | 0.042 | 2.5% | 0.043 | 0.043 | 0.465 | 0.436 | 0.041 | 0.059 |
| 5.0% | 0.043 | 0.041 | 1.25% | 0.042 | 0.042 | 0.472 | 0.463 | 0.041 | 0.049 |
| 2.5% | 0.047 | 0.041 | 0.63% | 0.042 | 0.041 | 0.464 | 0.461 | 0.04 | 0.044 |
| 1.25% | 0.321 | 0.269 | 0.31% | 0.289 | 0.301 | 0.457 | 0.461 | 0.04 | 0.043 |
| 0.63% | 0.502 | 0.481 | 0.16% | 0.482 | 0.437 | 0.483 | 0.488 | 0.041 | 0.041 |
| 0.31% | 0.539 | 0.526 | 0.08% | 0.552 | 0.513 | 0.48 | 0.479 | 0.042 | 0.041 |
| 0.16% | 0.499 | 0.532 | 0.04% | 0.507 | 0.507 | 0.483 | 0.482 | 0.042 | 0.042 |
| Empty | 0.047 | 0.047 | Empty | 0.047 | 0.047 | 0.049 | 0.048 | 0.048 | 0.048 |

Figure 1:
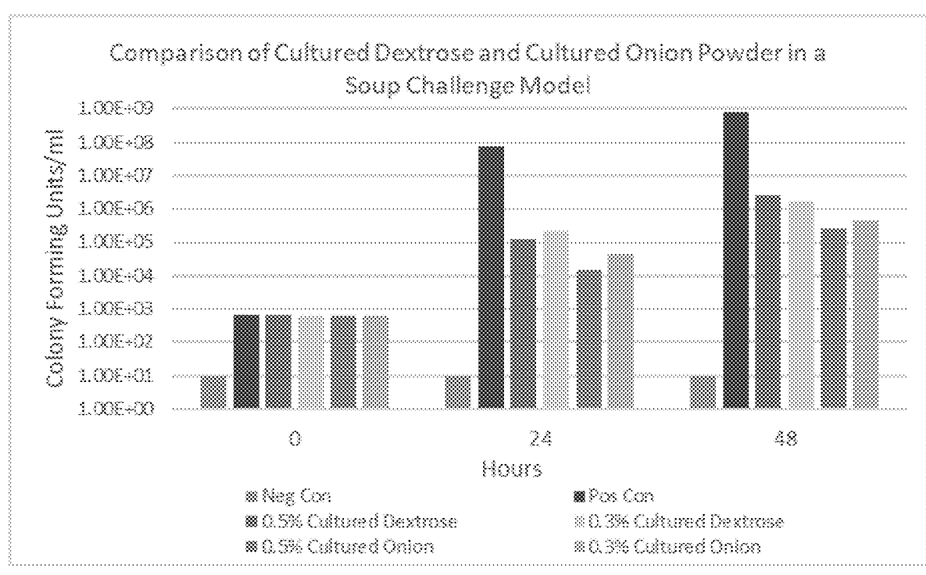
FIG. 1 shows a comparison of a cultured dextrose fermentate and a cultured onion powder fermentate in a model food system.

Example 11: Utility as an Ingredient to Preserve Food in a Challenge Model System To demonstrate the utility of cultured fruit and vegetable products as food preservatives, samples of the powdered onion fermentate were tested with samples of commercial cultured dextrose. One typical application for cultured dextrose products like these is in refrigerated soups. To model a soup system, 50 ml of unsalted commercial chicken broth was added to 125 ml Erlenmeyer flasks. The treatments indicated in table 15 below were added to the six flasks. After the addition of the treatments all of the flasks were autoclaved following standard lab procedures. Once cooled, the flask were inoculated with a mixed overnight cultures of *Lactobacillus graminis* and *Lactobacillus corinymformis* to a final concentration of ~5×10^2 CFU/ml. The flasks were placed in a shaking (150 rpm) incubator at 32° C. The combination of the elevated temperature (32° C. vs 4° C.) as well as the addition of microbial contamination makes this a robust challenge for the preservatives. All flasks were sampled at 0, 24 and 48 hour time points for enumeration of lactic acid bacteria in duplicate on DeMann, Rogosa, Sharpe (MRS) agar. The data is reported in FIG. 1. Both the commercial cultured dextrose product and the cultured onion product performed better than the inoculated control with no preservative with no significant difference seen between the 0.3% or 0.5% usage rate. The data clearly demonstrates that sufficient antimicrobial activity can be generated using these fruit and vegetable powders to produce a final product that is effective in controlling microbes in a food.

TABLE 25

Treatments used in the food spoilage model

| Variable | Treatment | Usage rate | Challenged |
|---|---|---|---|
| 1 | Negative Control | 0.0% | NO |
| 2 | Positive Control | 0.0% | YES |
| 3 | Cultured Dextrose | 0.5% | YES |
| 4 | Cultured Dextrose | 0.3% | YES |
| 5 | Cultured Onion | 0.5% | YES |
| 6 | Cultured Onion | 0.3% | YES |

We claim:

1. A method for producing a fermentate comprising:
    (a) obtaining a fruit or vegetable extract;
    (b) treating the fruit or vegetable extract with a hydrolytic enzyme;
    (c) mixing the fruit or vegetable extract with a fermenting microorganism, water, and a growth media capable of supporting the growth of the fermenting microorganism to produce a liquid composition;
    (d) incubating the liquid composition at a controlled temperature and a controlled pH to produce a fermentate; and
    (e) isolating the fermentate from the liquid composition, wherein the fermentate is devoid of viable cells wherein the fermentate has the ability to inhibit the growth of a contaminating microorganism by 100% when diluted to less than 5% (w/v).

2. The method of claim 1, wherein the hydrolytic enzyme is selected from the group consisting of a cellulase, a hemicellulase, a glucanase, a xylanase, and an amylase, and any combinations thereof.

3. The method of claim 1, further comprising a step of evaporating the fermentate to produce a second fermentate.

4. The method of claim 3, further comprising a step of spray-drying the second fermentate to produce a powdered fermentate.

5. The method of claim 1, further comprising a step of clarifying the fruit or vegetable extract.

6. The method of claim 5, wherein the fruit or vegetable extract is clarified prior to the step of mixing the fruit or vegetable extract with a fermenting microorganism, water, and a growth media.

7. The method of claim 1, wherein the fruit or vegetable extract is selected from the group consisting of onion extract, sweet potato extract, celery extract, carrot extract, chick pea extract, tomato extract, spinach extract and apple extract, and any combinations thereof.

8. The method of claim 1, wherein the fermenting microorganism is selected from the group consisting of a *Lactococcus* species, a *Lactobacillus* species, a *Streptococcus* species, a *Pediococcus* species, a *Propionibacterium* species, and any combinations thereof.

9. The method of claim 8, wherein the fermenting microorganism is selected from the group consisting of *Lactococcus lactis, Lactobacillus acidophilus, Lactobacillus plantarum, Lactobacillus reuteri, Propionibacterium freudenreichii, Propionibacterium acidipropionici, Lactobacillus brevis, Lactobacillus sakei, Pediococcus acidilactici*, and any combinations thereof.

10. The method of claim 1, wherein the controlled temperature is between about 10° C. and about 50° C.

11. The method of claim 1, wherein the controlled pH is between about 3 and about 10.

12. The method of claim 1, wherein the step of mixing further comprises mixing with a fermented yeast extract.

13. The method of claim 1, wherein the fermentate includes a cellular mass component comprising at least one metabolite selected from the group consisting of lactic acid, lactate, propionic acid, acetic acid, and ethanol, and any combinations thereof.

* * * * *